United States Patent [19]
Rattner

[11] Patent Number: 5,792,078
[45] Date of Patent: Aug. 11, 1998

[54] THERAPY APPARATUS WITH AN OPTICAL POSITIONING UNIT

[75] Inventor: Manfred Rattner, Grossenseebach, Germany

[73] Assignee: Siemens Aktiengesellschaft, Munich, Germany

[21] Appl. No.: 840,878

[22] Filed: Apr. 17, 1997

[30] Foreign Application Priority Data

Apr. 18, 1996 [DE] Germany ............... 196 15 342.5

[51] Int. Cl.⁶ ..................................................... A61N 7/00
[52] U.S. Cl. ........................................... 601/2; 600/427
[58] Field of Search .......................... 601/2–4; 600/427, 600/439, 476

[56] References Cited

U.S. PATENT DOCUMENTS

| | | |
|---|---|---|
| 3,237,623 | 3/1966 | Gordon. |
| 4,697,588 | 10/1987 | Reichenberger. |
| 4,928,672 | 5/1990 | Grasser et al. ................. 601/4 |
| 5,065,762 | 11/1991 | Ifflaender et al. .............. 601/4 |
| 5,488,951 | 2/1996 | Bauer et al. ................... 601/4 |
| 5,492,126 | 2/1996 | Hennige et al. ............. 600/439 |
| 5,583,901 | 12/1996 | Reitter et al. ................. 378/4 |

FOREIGN PATENT DOCUMENTS

PS 38 35 318  6/1990  Germany.
OS 41 20 074  1/1992  Germany.

*Primary Examiner*—Ruth S. Smith
*Attorney, Agent, or Firm*—Hill & Simpson

[57] ABSTRACT

A therapy apparatus with a source of acoustic waves has a light-transparent region, and an optical arrangement for obtaining image information from a body surface of a patient to be treated. The beam path of the optical arrangement runs through the light-transparent region of the source of acoustic waves. The optical arrangement is connected to an arrangement for the graphic display of the obtained image information.

7 Claims, 2 Drawing Sheets

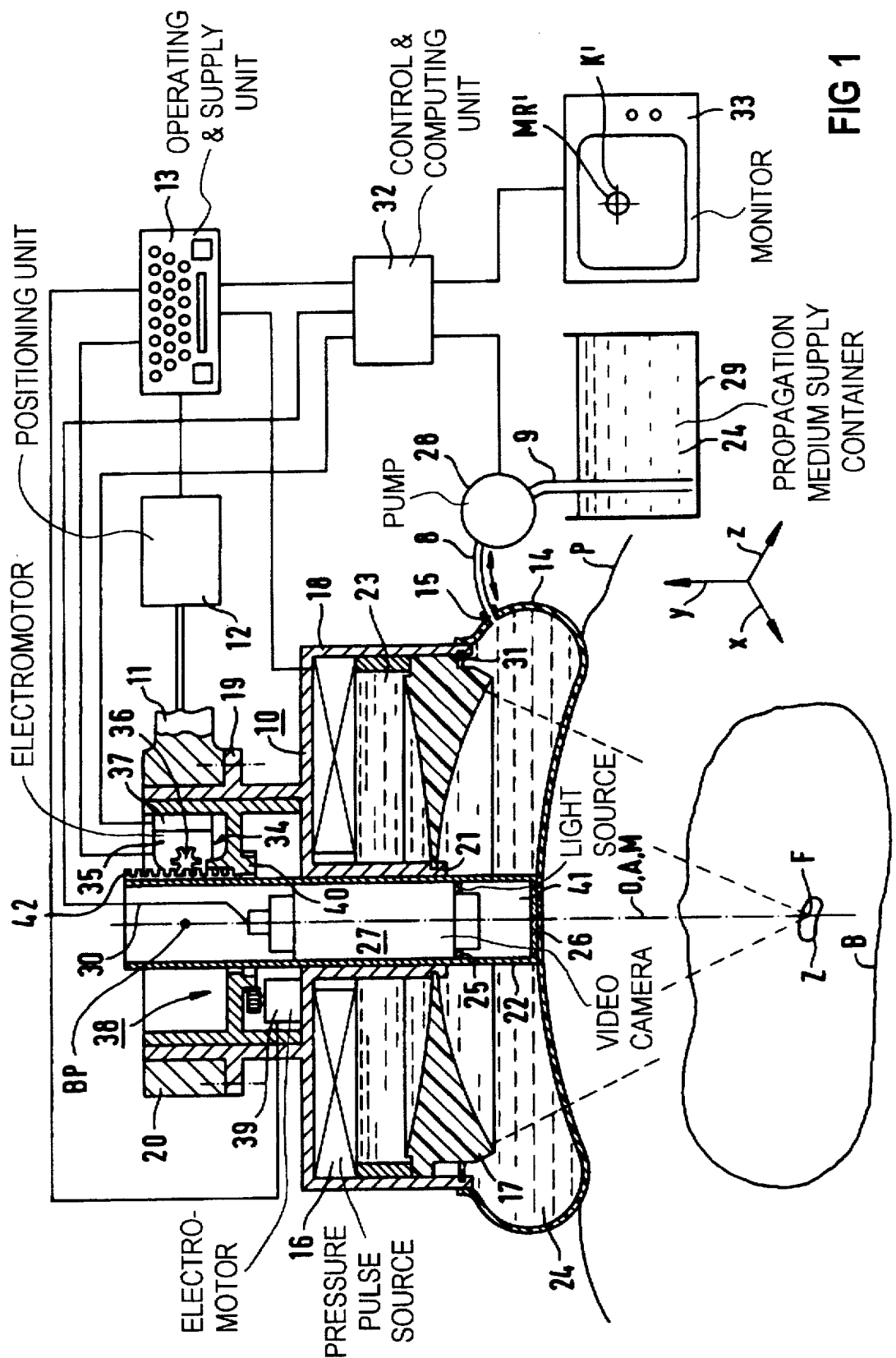

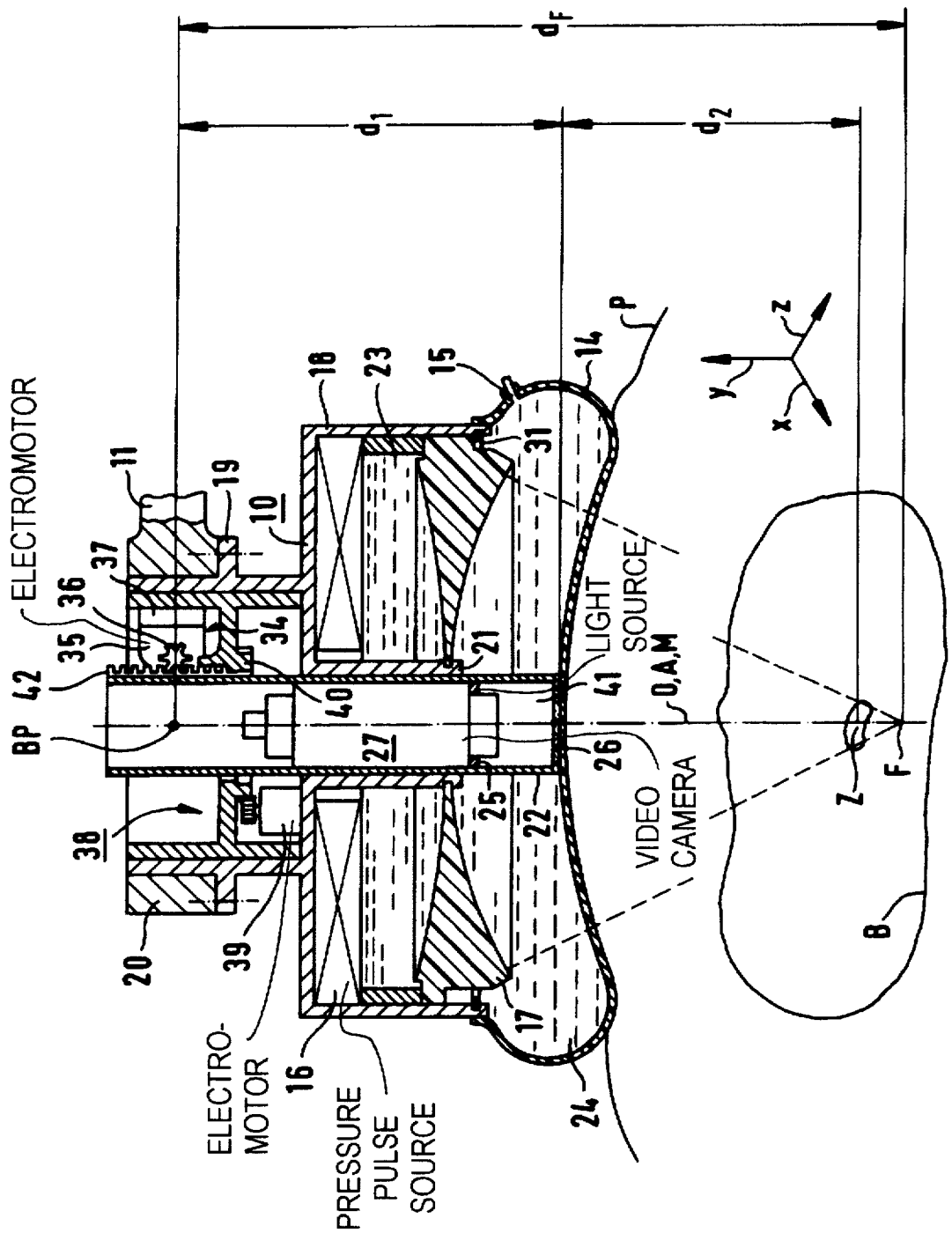

THERAPY APPARATUS WITH AN OPTICAL POSITIONING UNIT

BACKGROUND OF THE INVENTION

1. Field of the Invention

The present invention is directed to a therapy apparatus with a source of acoustic waves, with means for obtaining image information and with means for the graphic display of the obtained image information.

2. Description of the Prior Art

A therapy apparatus of the above general type is known for example, from U.S. Pat. No. 3,237,623, for operating on the eye in order to destroy groups of cells that have a detrimental effect on the patient's vision. An ultrasound location unit is used to detect the tissue to be destroyed, and the distance of the tissue to be destroyed from the inner and the outer surface of the wall of the eye is determined. It is also possible to locate the exact point on the inner surface of the eye under which the tissue to be destroyed is located, using an ophthalmoscope housed in the source of acoustic waves. In this way, the tissue to be destroyed is optically identified, and the effects of the radiation on the tissue to be destroyed are observed during treatment. The ophthalmoscope thereby serves above all for the identification of tissue and the observation of the progress of the treatment.

Therapy apparatuses of the above type are also currently used in pain therapy in order to cause focused acoustic waves to act on a painful body region of a patient, whereby as a rule the pain center, i.e. the point of maximum pain, is acted upon with the focused acoustic waves. As a result of the effect of the focused acoustic waves, the patient is relieved of pain at least for a certain period of time following the treatment. In the preparation phase of the treatment, the treating physician generally looks for the pain center in the body region indicated as painful by the patient, by acting on the indicated body region with weak focused acoustic waves and moving the source of acoustic waves systematically over the body region indicated by the patient while shifting the focus zone of the acoustic waves. The patient informs the physician how strong the feeling of pain is for the momentary position of the source, or the focus zone, of the acoustic waves. The optimal position, in which the pain center is located in the focus zone of the acoustic waves, is found when the sensation of pain is at its maximum.

During the orientation of the focus zone to the pain center, the means for obtaining image information contained in therapy apparatuses of the above type, and the means for graphic representation of the image information obtained (usually an ultrasound location unit), represent for the most part only an aid to orientation, since the pain center itself is often not visible in the obtained image information. The simplification of the orientation process that can be achieved by the means for obtaining image information and the means for graphic representation of the obtained image information is not sufficiently high in relation to the costs incurred due to these means, so that the possibility of doing without such means entirely is a factor which must be taken into consideration.

A therapy apparatus with a source of acoustic waves and with ultrasound units and/or X-ray location units are known for example from German OS 44 00 997 and German PS 38 35 318.

A therapy apparatus with a means for monitoring and controlling the position of the body of a patient during a treatment with focused acoustic waves is known from German OS 41 20 074. After positioning the source of acoustic waves relative to the body of the patient, a cross for example, is projected outside the body zone to be treated onto the body surface of the patient, and is marked e.g. with a felt marker. If the marking and the projected cross no longer coincide during the treatment of the patient with acoustic waves, the treatment is interrupted and the patient and the source are reoriented relative to one another.

SUMMARY OF THE INVENTION

An object of the present invention is to provide a therapy apparatus of the general type described above wherein the source of acoustic waves can be oriented relative to the body region to be treated in a simple and economical manner.

This object is achieved in accordance with the principles of the present invention in a therapy apparatus with a source of acoustic waves having a light-transparent region with optical means for obtaining image information from the body surface of a patient to be treated, the beam path of the optical means running through the light-transparent region of the source of acoustic waves, and with means for the graphic display of the image information obtained. The invention is based on the recognition that the physician can easily and rapidly determine the approximate position of the pain center by scanning the body region indicated by the patient, and can mark the position of the pain center on the body surface of the patient, e.g. by means of a cross applied with a grease pencil. Using the means for obtaining image information and the means for the graphic display of the obtained image information, the physician orients the source of acoustic waves onto this cross in such a way that the acoustic axis of the source runs at least approximately through the cross, and thereby through the pain center. The subsequent final orientation of the source of acoustic waves, and thus also the final orientation of the focus zone of acoustic waves, onto the pain center with the cooperation of the patient is considerably simpler and considerably shorter in comparison to known systems, and does not require costly means for obtaining image information, e.g. in the form of an ultrasound location unit. It is thereby important that the source have a light-transparent region, since otherwise the cross would be hidden by the source itself during the application of the source to the body surface, and would not be visible to the means for obtaining image information.

In a preferred embodiment of the invention the therapy apparatus has a mark arranged on the acoustic axis of the source, this mark being recorded by the means for obtaining image information, which are preferably located in the light-transparent region of the source, and is displayed by the means for the graphic display of the obtained image information. The positioning of the source relative to the body of the patient then ensues such that in the image information, the image of the mark arranged on the acoustic axis coincides on the graphic display means with the image of the cross made on the body surface of the patient by the physician. In this way it is ensured that the acoustic axis of the source of acoustic waves runs through the region to be treated of the patient and at least approximately through the pain center.

According to a further, preferred embodiment of the invention, a video camera is used as the optical means for obtaining image information, preferably having an additional light source. Video cameras represent economical and technologically suitable means for obtaining images and identifying optical markings, e.g. a cross, on the body surface of a patient. Since large therapy heads (which, in order to introduce acoustic waves into a body region of a patient, lie on the patient during treatment via a flexible, light-transparent coupling membrane that seals a chamber filled with an acoustic medium of propagation) can reduce the incidence of light into the region recorded by the video camera despite the light-transparent coupling membrane, the additional light source is advantageous for obtaining informative images of the body surface of the patient.

According to a variant of the invention, the means for obtaining image information are constructed so as to be removable from the region of the source of acoustic waves that houses the means for obtaining image information. This permits the optional use of other means, e.g. an eyepiece, or the video camera.

According to another embodiment of the invention, a monitor is used for the display of the image information obtained. Television monitors, or computer monitors connected to a computer with a corresponding graphics card with a video input, can be used. It has proved particularly advantageous to employ a monitor already present in the physician's practice so that additional costs for the purchase of a corresponding monitor can be avoided.

DESCRIPTION OF THE DRAWINGS

FIG. 1 shows an inventive therapy apparatus in a partly sectional, partly schematic representation.

FIG. 2 shows the therapy apparatus according to FIG. 1 in a partly sectional representation with distance indications.

DESCRIPTION OF THE PREFERRED EMBODIMENTS

As shown in FIG. 1, a therapy apparatus according to the invention has a source of acoustic waves generally designated 10, attached via a mount 11 to a positioning unit 12 (indicated only schematically). The positioning unit 12 allows positioning of the source 10 in the directions of the x, y, z axes of the spatial coordinate system indicated in FIG. 1. An operating and supply unit 13 is connected to this positioning unit 12, the operating and supply unit 13 containing all the components required for the operation of the source 10, and being provided with a keyboard for operator-controlled functioning of the therapy apparatus. The source 10 contains a central light-transparent region, described in more detail below, which lies on the body surface of a patient P with a likewise light-transparent coupling membrane 14, in order to enable the introduction of focused acoustic waves, produced during the operation of the therapy apparatus, into the body of the patient P, who is experiencing e.g. pain in a body region B.

As can be seen in FIG. 1, the source 10 of focused acoustic waves contains an electromagnetic pressure pulse source 16 (not shown in more detail) and an acoustic focusing lens 17. The focusing lens 17 focuses the pressure pulses emitted by the pressure pulse source 16 on a focus F, which in practice is a spatial (3D) focus zone. The focus F lies on the acoustic axis A of the source 10, which corresponds to the mid-axis M of the source 10. The source 10 is fashioned in approximately rotationally symmetrical fashion relative to the mid-axis M. The pressure pulse source 16 and the focusing lens 17 are contained in a housing 18 that is sealed in a liquid-tight manner at its end remote from the pressure pulse source 16 by means of the elastic, flexible coupling membrane 14. The pressure pulse source 16 is, for example an electromagnetic pressure pulse source, of the type described with respect to construction and function in European Application 0 188 750 and in European Application 0 301 630. The high-voltage pulse generator required for the operation of the pressure pulse source 16 is a component of the operating and supply unit 13, with which the pressure pulse source 16 is connected via a corresponding line.

At its other end adjacent to the pressure pulse source 16, the housing 18 has a mounting flange 19 that serves to fasten the source 10 on a mounting ring 20 of the mount 11 by means of screws (in FIG. 1 only the center lines of two screws are shown, in dashed lines).

The space located between the pressure pulse source 16 and the focusing lens 17, and the space located between the focusing lens 17 and the coupling membrane 14, are each filled with an acoustic propagation medium. In the embodiment described, both spaces contain the same acoustic propagation medium, namely water 23 or 24. In the embodiment described, the two spaces filled with water 23 and 24 are separated from one another by the focusing lens 17, however, they can alternatively be connected with one another, in particular if both spaces contain the same acoustic propagation medium.

The focusing lens 17 is a biconcave lens of solid material, made of a material (e.g. polystyrene) in which the speed of sound is greater than in the water 23 and 24 provided as an acoustic propagation medium. The focusing lens 17 is held in the housing 18 by a mounting ring 31.

The coupling membrane 14 has an opening in the shape of a connecting sleeve 15. A tube line 8 connects the connecting sleeve 15 of the coupling membrane 14 with a pump 28, which is in turn connected with a supply container 29 via a tube line 9, the supply container 29 being partially filled with the acoustic propagation medium, i.e., water 24. The pump 28 can be operated so that, as needed, it pumps water 24 into the space between the focusing lens 17 and the coupling membrane 14, and also pumps water 24 out of the space between the focusing lens 17 and the coupling membrane 14. In this way, the volume of the space between the focusing lens 17 and the elastic and flexible coupling membrane 14 can be optionally enlarged or made smaller.

A cup-like tube 22 is set into an opening 41 of a cylindrically tubular inner wall 21 of the housing 18, the tube 22 being fashioned from a light-transparent material, e.g. Plexiglas®, at least in the region of its base 26. The tube 22 can be displaced axially in the opening 41 of the inner wall 21, and is held therein in a liquid-tight manner, for which purpose sealing means (not shown in FIG. 1) may be provided. A video camera 27 (not shown in more detail in FIG. 1) is set into the tube 22, at a distance from its base 26. The optical axis O of the video camera 27 coincides with the acoustic axis A of the source 10. The focal length of the lens of the video camera 27 can be set by means of a control and computing unit 32, connected to the video camera via a video signal line 30. The lens of the video camera 27 is additionally surrounded by an annular light source 25, so that usable video exposures can be obtained when ambient light is insufficient. The light source need not necessarily be fashioned with an annular shape. The base 26 of the tube 22 is additionally provided with an optical mark that lies on the acoustic axis A of the source 10.

In the present exemplary embodiment, the control and computing unit 32 is a commercially available PC, to which a monitor 33 and a keyboard (not shown in FIG. 1) are connected.

The central opening 41 of the source 10 which is present inside the inner wall 21, in which opening the tube 22 is located, represents the aforementioned light-transparent region, from which the water 24 is expelled by means of the tube 22 in order to avoid negative influences on the image quality. For this purpose, when the source 10 is applied to the body surface of the patient P indicated in FIG. 1, the tube 22 is displaced far enough into the opening 41 of the inner wall 21 so that its base 26 lies on the body surface of the patient P with the coupling membrane 14 interposed therebetween. For this purpose, an additional positioning unit 34 is provided, by means of which the tube 22 can be displaced in the axial direction. The positioning unit 34 contains an electromotor 35 provided with a pinion 36, which operates together with a rack 42 provided on the tube 22. A position sensor 37 is allocated to the positioning unit 34, the sensor 37 supplying a signal that corresponds to the axial position of the tube 22, which signal indicates the distance $d_1$ (see FIG. 2) of the base 26 of the tube 22 from a reference point BP that lies on the acoustic axis A of the source 10. This signal is supplied to the control and computing unit 32. The distance $d_F$ of the focus F from the reference point BP of the source 10 is stored in the operating and supply unit 13 of the source 10, and is provided to the control and computing unit 32 via a control line.

The tube 22 additionally can be rotated around the acoustic axis A by means of a positioning unit 38. The positioning unit 38 contains an electromotor 39 provided with a pinion, operating together with a carrier provided with a toothed ring 40, the carrier being rotatable within the housing 18, and being connected in a torsionally resistant manner with the tube 22 such as by a lower extension of the rack 42 that projects into a groove of the carrier in the manner of a keyed engagement which still allows relative vertical movement between the carrier and the tube 22.

The electromotors 35 and 39 of the positioning units 34 and 38 are connected with the operating and supply unit 13 via corresponding lines.

For the treatment of the patient, the patient is first placed in a suitable position on a treatment table (not shown). The treating physician first scans the body region indicated as painful by the patient, and marks (e.g. with a cross, not visible in FIGS. 1 and 2) the point on the body surface of the patient under which the pain center Z is located according to the patient's indications. Next, the patient is oriented on the treatment table in such a way that the body region beneath the body surface marked with a cross is located approximately in the region of the acoustic axis A of the source 10. On the basis of the video signals of the video camera 27, which are displayed on the monitor 33 connected to the control and computing unit 32, the treating physician can orient the source 10 using the operating and supply unit 13 so that the images K' and MR' (the cross made by the physician on the body surface of the patient P and the optical mark of the base 26 of the tube 22, respectively) come into coincidence on the monitor 33. The acoustic axis A of the source 10 then runs through the cross, and at least approximately also through the pain center Z of the patient P.

In order to position the focus F of the source 10 so that its distance from the body surface is at least approximately equal to the distance of the pain center Z from the body surface, the physician proceeds as follows. The physician first determines (e.g. by estimation or by using ultrasound diagnosis) the distance $d_2$ of the pain center Z from the body surface of the patient P, which distance remains at least approximately constant during the treatment. Then, by changing the distance $d_1$ of the reference point BP from the base 26 of the tube 22, which thereby lies on the body surface of the patient P, the physician sets the distance of the focus F of the source 10 from the body surface so that it corresponds to the distance of the pain center Z from the body surface. For this purpose, the current distance values $d_1$, $d_2$ and $d_F$ according to FIG. 2 are displayed on the monitor 33 next to the video images of the video camera 27, but generally only the distance $d_1$ is altered.

If, as in the present exemplary embodiment according to FIG. 2, the focus F of the source 10 comes to lie behind the pain center Z of the patient, the distance $d_1$ must be increased until the sum of the distances $d_1$ and $d_2$ is equal to the distance $d_F$. When this is the case, the focus F of the pressure pulses is located in the pain center Z of the patient. During the setting of the focus position, the pump 28 is driven by the control and computing unit 32 so that it pumps water 24 out of the supply container 29 via the tube lines 8 and 9 into the space between the focusing lens 17 and the coupling membrane 14, thereby enlarging this volume, and the source 10 moves away from the body surface. At the same time, the tube 22 is guided into the cylindrically tubular inner wall 21 of the housing 18 via the positioning unit 34, possibly limited by the force acting between the tube 22 and the body surface, so that its base 26 always lies snugly on the body surface of the patient P. The control and computing unit 32 is thus always provided with the current distance $d_1$ via the position sensor 37. The pumping process remains active until, due to water 24 being supplied into the space between the focusing lens 17 and the coupling membrane 14, the source is moved away from the body surface by the increase in volume of the space until the sum of the distances $d_1$ and $d_2$ is equal to the distance $d_F$.

If, after the positioning of the source 10 over the pain center of the patient P, the focus F of the source 10 comes to lie in front of the pain center of the patient P, in this case water 24 is pumped out of the space between the focusing lens 17 and the coupling membrane 14 into the supply container 29, so that the volume of the space between the focusing lens 17 and the coupling membrane 14 becomes smaller, and the focus F of the source 10 moves toward the pain center Z of the patient. The tube 22 is thereby guided so that the distance $d_1$ of the base 26 of the tube 22 from the reference point BP continuously becomes smaller, until the sum of the distances $d_1$ and $d_2$ is again identical with the distance $d_F$ of the focus F from the reference point BP of the source 10.

If, in the manner described, the images K' and MR' of the cross and the mark on the base 26 of the tube 22 are brought into coincidence, and the required distance of the focus F from the body surface is set, then, with the cooperation of the patient, the physician carefully positions the source 10 relative to the body of the patient P, with the emission of focused acoustic waves of reduced intensity, until the focus F is actually located in the pain center Z. The actual treatment can now begin.

In addition, the optical mark on the base 26 of the tube 22 is not required if a mark identifying the position of the acoustic axis A is electronically mixed into the video image, in a known manner.

In the described embodiment, in the opening 41 of the inner wall 21 of the housing 18 the tube 22 and therewith the video camera 27, are moved around the acoustic axis A by the positioning unit 38, and are moved in the direction of the acoustic axis A by the positioning unit 34. Of course, the tube 22, and therewith the video camera 27, can alternatively be moved manually around the acoustic axis A or along the acoustic axis A. The possibility of rotating the tube 22 around the acoustic axis A can be omitted, since it is not absolutely required in order to bring the image K' of the cross and the image MR' of the mark on the base 26 of the tube 22 into coincidence.

In addition, the video camera 27 can be connected directly to a television monitor. In this case, the position sensor 37 is connected directly to the operating and supply unit 13 of the source 10, which unit carries out the distance calculations and drives the pump 28 correspondingly.

In the described embodiment, the focusing lens 17 has a fixed focal length, however, it is also possible to use a variable-focus lens, i.e. a lens with an adjustable focal length.

If necessary, the tube 22 can be removed from the source 10 of acoustic waves, but it must be ensured that a corresponding tube is introduced into the source 10 in a way not shown, in order to prevent loss of water 24.

The tube 22 need not necessarily be fashioned with a cup-like shape, but rather can, for example, be constructed with a semi-circular shape, particularly at its base. Under some circumstances, however, corresponding measures must then be taken to ensure that there is no negative influence on the image quality of the video images.

In addition, the coupling membrane 14 need not be provided with only one sleeve 15 for the supply and removal of water 24, and with only one pump 28. Rather, for the supply and removal of water to the space between the focusing lens 17 and the coupling membrane 14, several pumps, sleeves, tube lines, and, if useful, valves that prevent backflow of water, can be provided.

If the two water-filled spaces 23 and 24 of the source are not separated from one another (as in the present embodiment) by the focusing lens 17, the housing 18 of the source 10 can be provided with corresponding supply and removal sleeves in the region of the space between the pressure pulse source 16 and the focusing lens 17. Water 23 or 24, for increasing or decreasing the volume of the space between the focusing lens 17 and the coupling membrane 14, would then be supplied or removed via such sleeves.

In the embodiment described above, the source 10 contains an electromagnetic pressure pulse source. The inventive therapy apparatus can, however, alternatively employ a different type of pressure pulse source, e.g., a pressure pulse source that operates piezoelectrically. It is also possible to provide other sources of acoustic waves in place of a pressure pulse source, e.g., an ultrasound source, which produces ultrasound in the form of continuous sound, ultrasound bursts or ultrasound pulses.

Furthermore, it is also possible to carry out the orientation of the source 10 over the body region of the patient P marked with a cross by the physician manually, rather than with the operating and supply unit 13.

Moreover, the "depth measurement" for the determination of the distance $d_1$ of the reference point of the source 10 from the body surface of the patient P for setting the focus position can be omitted. In practice the focus zone Z is not punctiform, but instead generally has an oblong cigar-like shape. Therefore, after the optical positioning of the source 10 over the body region of the patient P marked with a cross, while focused acoustic waves of reduced intensity are emitted to the patient P, the physician can carefully and in a step-by-step fashion alter the distance of the source 10 from the body surface of the patient P, and thus the distance of the focus zone F from the pain center Z. This alteration preferably takes place along the acoustic axis A, and proceeds until the patient P informs the physician that the maximum sensation of pain has been achieved, and the focus zone F thus lies at least approximately at the pain center Z.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapy apparatus for treating a patient with acoustic waves acting at a selected body region within the patient, comprising:

a housing for exclusively extracorporeal placement relative to an external body surface of a patient;

a source of acoustic waves contained in said housing and having a light-transparent region;

optical means, disposed in said source of acoustic waves, for obtaining image information from an external body surface of a patient to be treated, said optical means having an optical beam path running through said light-transparent region of said source of acoustic waves; and means, connected to said optical means, for graphically displaying said image information obtained by said optical means for extracorporeally orienting said source.

2. A therapy apparatus as claimed in claim 1 wherein said means for obtaining image information are disposed in said light-transparent region of said source of acoustic waves.

3. A therapy apparatus as claimed in claim 1 wherein said source of acoustic waves has an acoustic axis, and said apparatus further comprising a mark disposed on said source of acoustic waves coinciding with said acoustic axis, said mark being recordable by said means for obtaining image information and being displayed by said means for graphically displaying said image information.

4. A therapy apparatus as claimed in claim 1 wherein said means for obtaining image information comprises a video camera.

5. A therapy apparatus as claimed in claim 4 wherein said video camera has a field of view, and said therapy apparatus further comprising a light source disposed in said housing for illuminating said field of view.

6. A therapy apparatus as claimed in claim 4 wherein said means for graphically displaying said image information comprises a video monitor.

7. A therapy apparatus as claimed in claim 1 further comprising means for removably mounting said means for obtaining information in said source of acoustic waves.

* * * * *